US005824093A

United States Patent [19]
Ray et al.

[11] Patent Number: 5,824,093
[45] Date of Patent: Oct. 20, 1998

[54] PROSTHETIC SPINAL DISC NUCLEUS

[75] Inventors: Charles D. Ray, Williamsburg, Va.; Eugene A. Dickhudt, New Brighton; Robert L. Assell, Mendota Heights, both of Minn.

[73] Assignee: RayMedica, Inc., Bloomington, Minn.

[21] Appl. No.: 870,866

[22] Filed: Jun. 6, 1997

Related U.S. Application Data

[63] Continuation-in-part of Ser. No. 638,306, Apr. 26, 1996, Pat. No. 5,674,295, which is a continuation of Ser. No. 324,142, Oct. 17, 1994, abandoned.

[51] Int. Cl.$^6$ .................................................. A61F 2/44
[52] U.S. Cl. ............................................................ 623/17
[58] Field of Search .............................. 623/17; 606/61

[56] References Cited

U.S. PATENT DOCUMENTS

| | | | |
|---|---|---|---|
| 3,867,728 | 2/1975 | Stubstad et al. | 3/1 |
| 3,875,595 | 4/1975 | Froning | 3/1 |
| 4,636,217 | 1/1987 | Ogilvie et al. | 623/17 |
| 4,772,287 | 9/1988 | Ray et al. | 623/17 |
| 4,904,260 | 2/1990 | Ray et al. | 623/17 |
| 4,932,969 | 6/1990 | Frey et al. | 623/17 |
| 5,047,055 | 9/1991 | Bao et al. | 623/17 |
| 5,171,280 | 12/1992 | Baumgartner | 623/17 |
| 5,192,326 | 3/1993 | Bao et al. | 623/17 |
| 5,246,458 | 9/1993 | Graham | 623/17 |
| 5,258,043 | 11/1993 | Stone | 623/66 |
| 5,306,307 | 4/1994 | Senter et al. | 623/17 |
| 5,306,308 | 4/1994 | Gross et al. | 623/17 |
| 5,306,309 | 4/1994 | Wagner et al. | 623/17 |
| 5,320,644 | 6/1994 | Baumgartner | 623/17 |

FOREIGN PATENT DOCUMENTS

| | | |
|---|---|---|
| 304305 | 5/1992 | European Pat. Off. |
| 2639823 | 12/1988 | France |
| 895433 | 1/1982 | U.S.S.R. |
| WO92/10982 | 7/1992 | WIPO |
| WO94/23671 | 10/1994 | WIPO |

OTHER PUBLICATIONS

Clinical Efficacy and Outcome in the Diagnosis and Treatment of Low Back Pain, specifically Chapter 21, Charles Dean Ray, *The Artificial Disc, Introduction, History and Socioeconomics,* 1992, pp. 205–225.

Primary Examiner—Michael J. Milano
Attorney, Agent, or Firm—Dicke, Billig & Czaga, P.A.

[57] ABSTRACT

An elongated, capsule shaped prosthetic spinal disc nucleus body for implantation into a human inter vertebral spinal disc, made of a hydrogel core and a constraining jacket surrounding the hydrogel core that permits the hydrogel core to deform and reform. The constraining jacket is configured to allow the hydrogel core to hydrate to a predetermined volume and will deform and reform in a desired fashion in response to various loads placed upon the spinal tract. The prosthetic spinal disc nucleus assists in restoring the natural physiology of the human intervertebral disc. By implanting two prosthetic spinal disc nuclei side-by-side into a damaged disc of a human spine, both height and motion can be maintained.

14 Claims, 9 Drawing Sheets

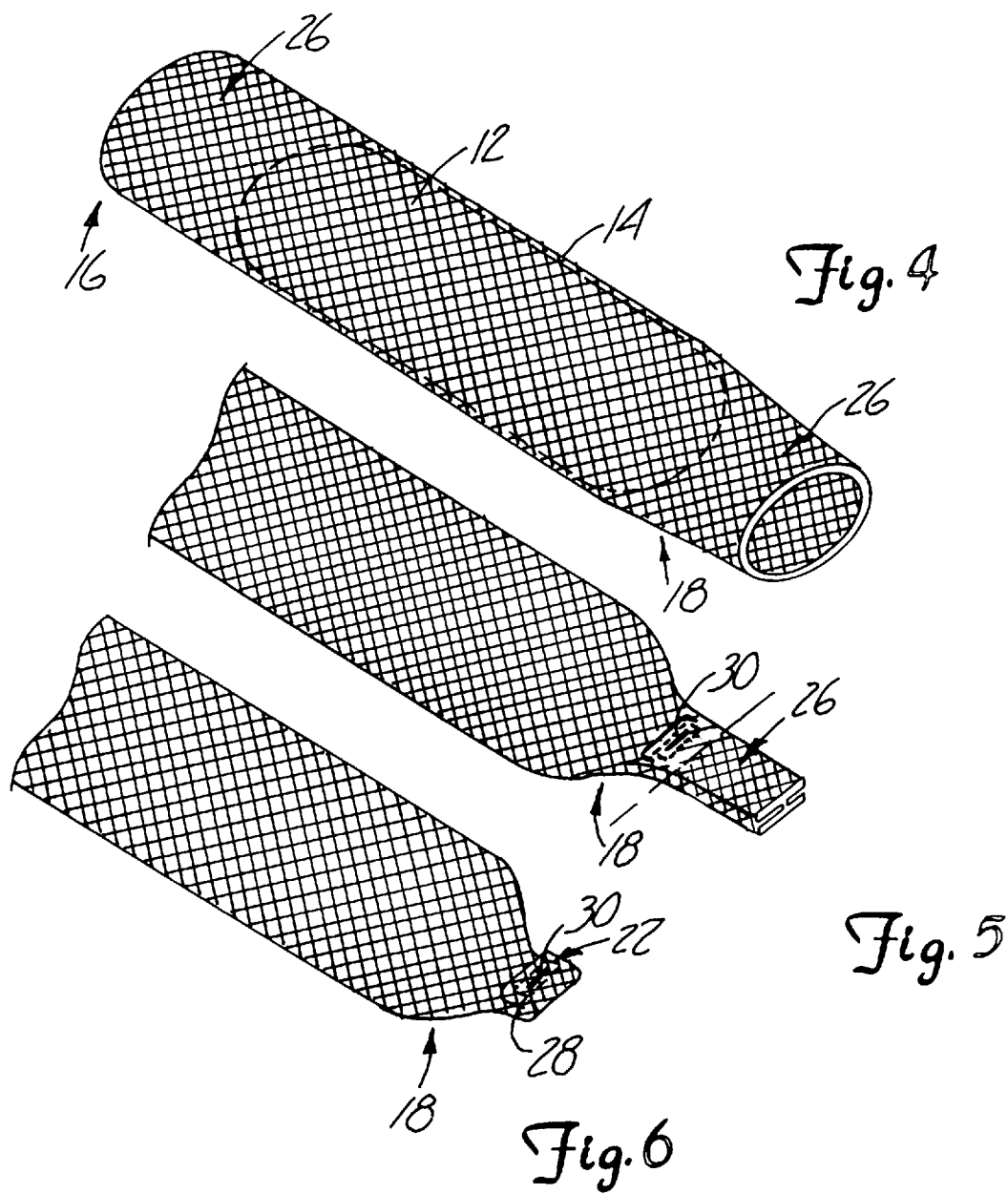

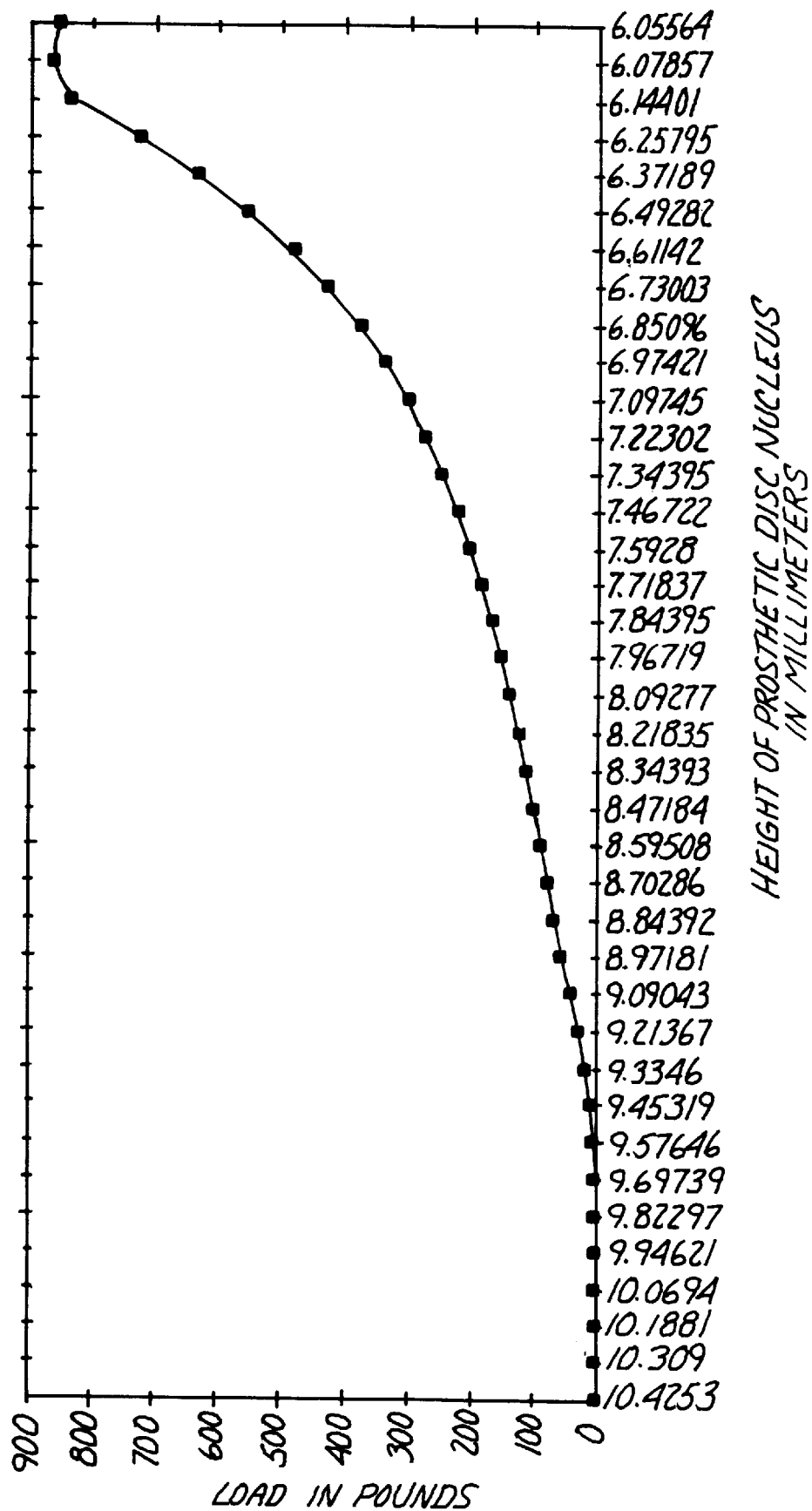

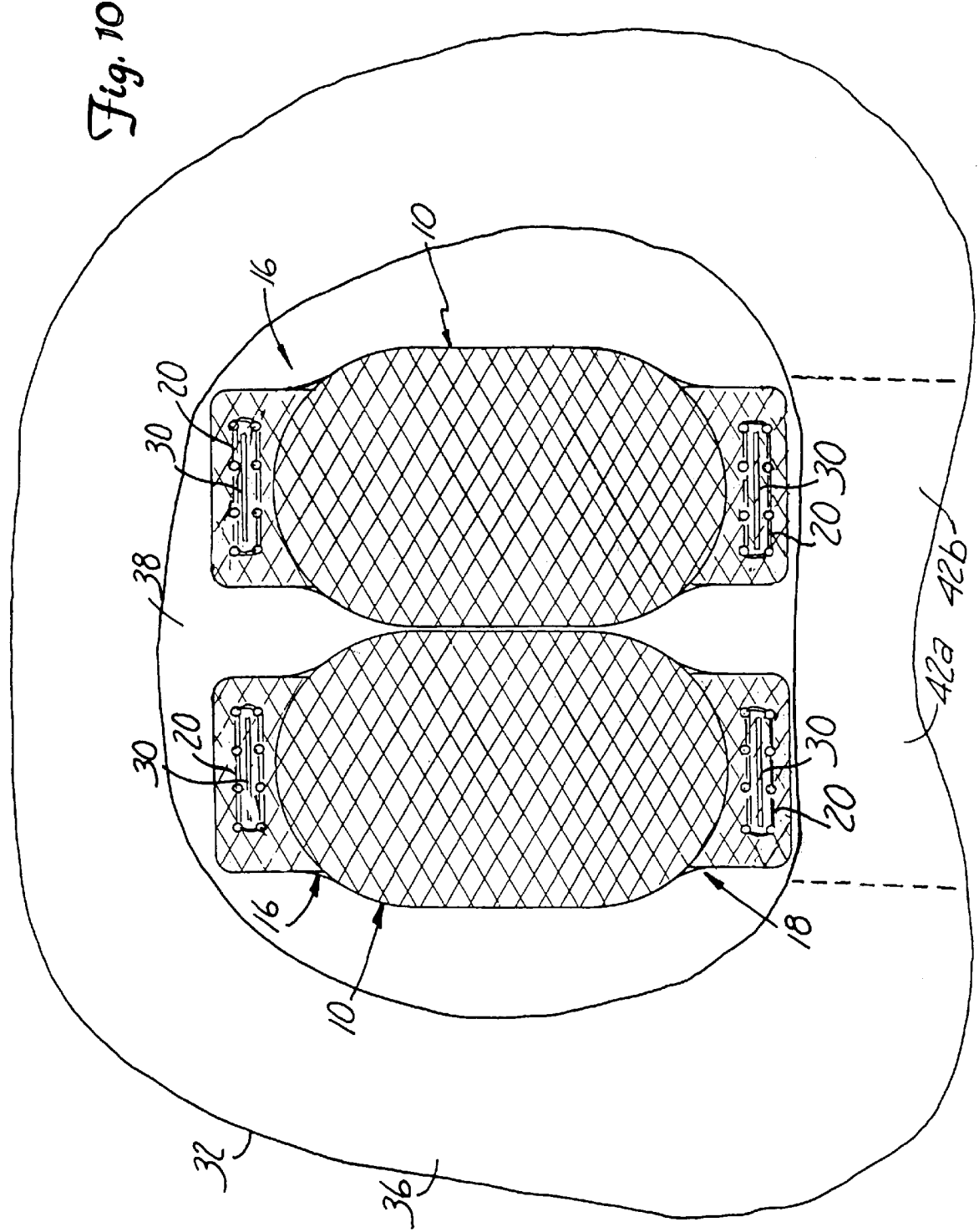

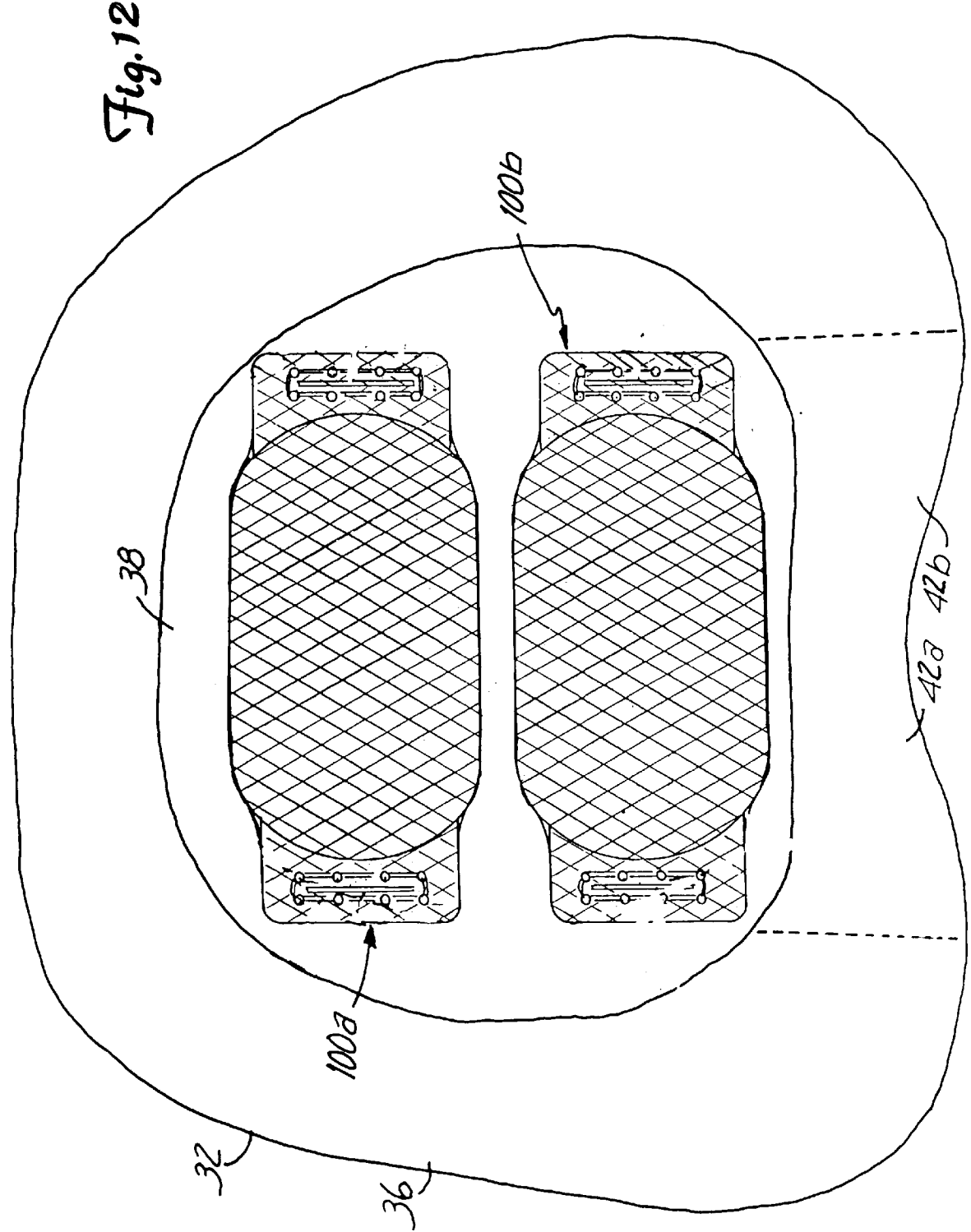

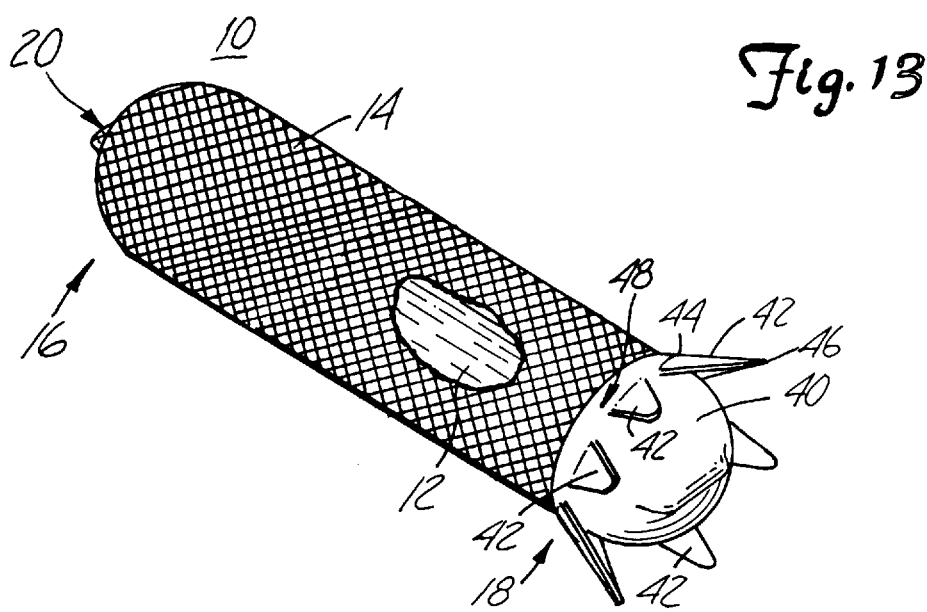

PROSTHETIC SPINAL DISC NUCLEUS

This is a continuation-in-part of application Ser. No. 08/638,306, filed on Apr. 26, 1996, now U.S. Pat. No. 5,674,295, which is a continuation of application Ser. No. 08/324,142, filed on Oct. 17, 1994, now abandoned.

BACKGROUND OF THE INVENTION

The present invention concerns a prosthetic spinal disc nucleus. More particularly it relates to an implantable capsule or pillow-shaped prosthetic disc nucleus having the ability to stimulate resumption of the natural physiology of a degenerated human disc.

The vertebrate spine is the axis of the skeleton upon which all of the body parts "hang". In humans, the normal spine has seven cervical, twelve thoracic and five lumbar segments. The lumbar spine sits upon the sacrum, which then attaches to the pelvis, in turn supported by the hip and leg bones. The bony vertebral bodies of the spine are separated by intervertebral discs, which act as joints but allow known degrees of flexion, extension, lateral bending and axal rotation.

The intervertebral disc primarily serves as a mechanical cushion between the vertebral bones, permitting controlled motions within vertebral segments of the axial skeleton. The normal disc is a unique, mixed structure, comprised of three component tissues: the nucleus pulposus ("nucleus"), the anulus fibrosus ("anulus") and two vertebral end plates . The two vertebral end plates are composed of thin cartilage overlying a thin layer of hard, cortical bone which attaches to the spongy, richly vascular, cancellous bone of the vertebral body. The end plates thus act to attach adjacent vertebrae to the disc. In other words, a transitional zone is created by the end plates between the malleable disc and the bony vertebrae.

The anulus of the disc is a tough, outer fibrous ring which binds together adjacent vertebrae. This fibrous portion, which is much like a laminated automobile tire, is generally about 10 to 15 millimeters in height and about 15 to 20 millimeters in thickness. The fiber layers of the anulus consist of fifteen to twenty overlapping multiple plies, and are inserted into the superior and inferior vertebral bodies at roughly a 40 degree angle in both directions. This configuration particularly resists torsion, as about half of the angulated fibers will tighten when the vertebrae rotate in either direction, relative to each other. The laminated plies are less firmly attached to each other.

Immersed within the anulus, positioned much like the liquid core of a golf ball, is the nucleus. The healthy nucleus is largely a gel-like substance having a high water content, and like air in a tire, serves to keep the anulus tight yet flexible. The nucleus-gel moves slightly within the anulus when force is exerted on the adjacent vertebrae with bending, lifting, etc.

The nucleus and the inner portion of the anulus have no direct blood supply. In fact, the principal nutritional source for the central disc arises from circulation within the vertebral body. Microscopic, villous-like fingerlings of the nuclear and anular tissue penetrate the vertebral end plates and allow fluids to pass from the blood across the cell membrane of the fingerlings and then inward to the nuclear tissue. These fluids are primarily body water and the smallest molecular weight nutrients and electrolytes.

The natural physiology of the nucleus promotes these fluids being brought into and released from the nucleus by cyclic loading. When fluid is forced out of the nucleus, it passes again through the end plates and then back into the richly vascular vertebral bodies. This cyclic loading amounts to daily variations in applied pressure on the vertebral column (body weight and muscle pull) causing the nucleus to expel fluids, followed by periods of relaxation and rest, resulting in fluid absorption or swelling by the nucleus. Thus, the nucleus changes volume under loaded and non-loaded conditions. Further, the tightening and loosening effect stimulates normal anulus collagen fibers to remain healthy or to regenerate when torn, a process found in all normal ligaments related to body joints. Notably, the ability of the nucleus to release and imbibe fluids allows the spine to alter its height and flexibility through periods of loading or relaxation. Normal load cycling is thus an effective nucleus and inner anulus tissue fluid pump, not only bringing in fresh nutrients, but perhaps more importantly, removing the accumulated, potentially autotoxic by-products of metabolism.

The spinal disc may be displaced or damaged due to trauma or a disease process. A disc herniation occurs when the anulus fibers are weakened or torn and the inner tissue of the nucleus becomes permanently bulged, distended, or extruded out of its normal, internal anular confines. The mass of a herniated or "slipped" nucleus tissue can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases causing the anulus to buckle in areas where the laminated plies are loosely bonded. As these overlapping laminated plies of the anulus begin to buckle and separate, either circumferential or radial anular tears may occur, potentially resulting in persistent and disabling back pain. Adjacent, ancillary spinal facet joints will also be forced into an overriding position, which may create additional back pain.

Whenever the nuclear tissue is herniated or removed by surgery, the disc space will narrow and may lose much of its normal stability. In many cases, to alleviate pain from degenerated or herniated discs, the nucleus is removed and the two adjacent vertebrae surgically fused together. While this treatment alleviates the pain, all discal motion is lost in the fused segment. Ultimately, this procedure places greater stresses on the discs adjacent to the fused segment as they compensate for the lack of motion, perhaps leading to premature degeneration of those adjacent discs. A more desirable solution would involve replacing in part or as a whole the damaged disc with a suitable prosthesis having the ability to complement the normal height and motion of a disc while simulating the natural disc physiology.

Restoring the nutrition-flushing cycle of a natural disc is important for a prosthetic spinal disc nucleus to be successful. Vascular circulation and nerve supply to the disc is limited to the outer layers of the anulus, never penetrating more than a few millimeters or about five of the plies. Most of the nutrition of the inner anulus and nucleus is provided by diffusion through the end plates of the vertebral bodies and by the important pumping action between the partially loaded and fully loaded conditions of the disc. If the nutritional cycle is impeded, a variety of degenerative changes may occur. Nutrition to the inner disc slowly ceases, resulting in intradiscal build-up of acids and toxins, and other changes. This is followed by nuclear and anular fiber degeneration, shrinkage of the nucleus, segmental laxity, spur formation, disc space collapse and perhaps spontaneous fusion. Additionally, significantly disabling back pain may develop.

Degenerated, painfully disabling interspinal discs are a major economic and social problem for patients, their families, employers and the public at large. Any significant means to correct these conditions without further destruction or fusion of the disc may therefore serve an important role. Other means to replace the function of a degenerated disc have major problems such as complex surgical procedures, which may require opening of the abdomen to install a large device that replaces the entire disc. Therefore, a substantial need exists for an easily implantable, prosthetic spinal disc nucleus which restores the size, load bearing ability and pumping action of a normal disc.

SUMMARY OF THE INVENTION

The invention provides an elongated prosthetic spinal disc nucleus for implantation deep inside a human disc space. The prosthesis is composed of a hydrogel core and a constraining jacket surrounding the hydrogel core.

The hydrogel core is an elongated cylinder having an oval shaped cross-section defining a major and minor axis. The hydrogel core is configured to imbibe fluids after implant, expanding as it hydrates.

The constraining jacket surrounds the hydrogel core and constrains expansion upon hydration. The jacket is flexible but inelastic, directing the hydrogel core to deform and reform in the minor axis. In a preferred embodiment, the jacket is porous and allows fluids to pass through to the hydrogel core.

The prosthetic spinal disc nucleus is configured such that in a hydrated, unloaded state, it has a length in the range of approximately 10 to 35 millimeters. Further, the hydrated, unloaded prosthetic spinal disc nucleus has a major axis diameter in the range of approximately 10 to 20 millimeters. Finally, the hydrated, unloaded spinal disc nucleus has a minor axis diameter which encompasses the natural height of the disc space, as defined by the vertebral end plates, in the range of approximately 5 to 15 millimeters.

The prosthetic spinal disc nucleus reestablishes near normal disc height and normal anulus position and function. Additionally, the prosthetic spinal disc nucleus will deform and reform primarily in the direction of the minor axis of the hydrogel core in response to physiological loads, providing necessary support to the discal area, tightening and loosening the anulus in a normal, health manner. Following implantation, the prosthetic spinal disc nucleus also works in concert with the remaining disc components to restore the natural physiology of a human disc. In response to the removal and exertion of compressive loads on the disc space, the restored disc will imbibe and expel fluids during the natural cyclic pumping of the discal area.

BRIEF DESCRIPTION OF THE DRAWINGS

FIGS. 4–6 illustrate steps of fabricating the prosthetic spinal disc nucleus of FIG. 1.

FIG. 7 is a graph showing a compression modulus of elasticity for the prosthetic spinal disc nucleus of the present invention following conditioning;

FIG. 10 is a top, sectional view of a human disc space having two prosthetic spinal disc nuclei implanted;

FIG. 12 is a top, sectional view of a human disc space having two prosthetic spinal disc nuclei in accordance with an alternative embodiment of the present invention;

FIG. 13 is a perspective view of an alternative embodiment of the prosthetic spinal disc nucleus which includes a tine assembly.

DETAILED DESCRIPTION OF THE PREFERRED EMBODIMENTS

Figure 1:
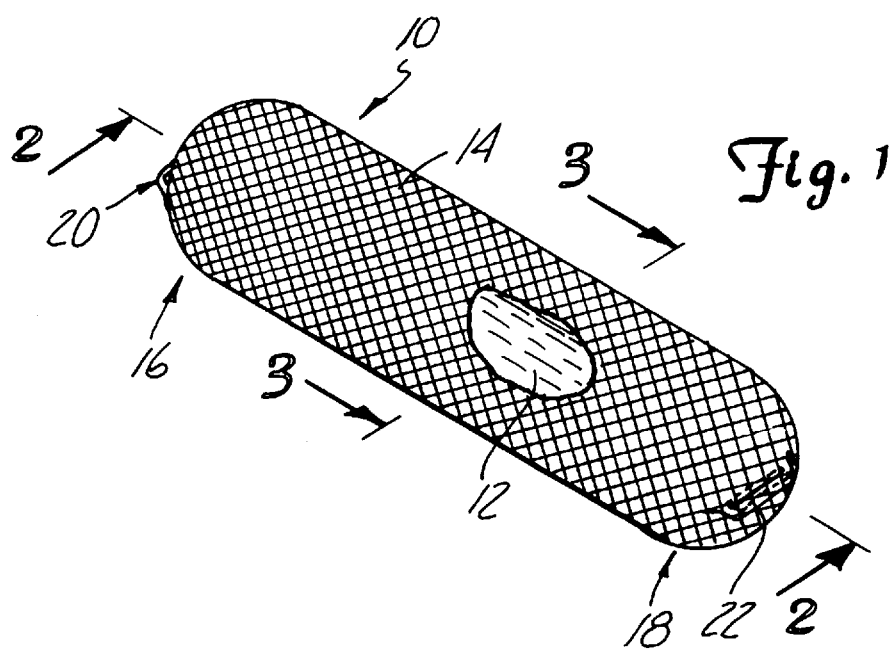
FIG. 1 is a perspective view of a prosthetic spinal disc nucleus, including a cutaway view showing a portion of a hydrogel core, in accordance with the present invention.

A preferred embodiment of a prosthetic spinal disc nucleus 10 is shown in FIG. 1. The prosthetic spinal disc nucleus 10 is comprised of a hydrogel core 12 and a constraining jacket 14. The prosthetic spinal disc nucleus 10 has an anterior end 16 and a posterior end 18. The constraining jacket 14 is secured around the hydrogel core 12 by an anterior closure 20 located at the anterior end 16 and a posterior closure 22 located at the posterior end 18.

Figure 2:
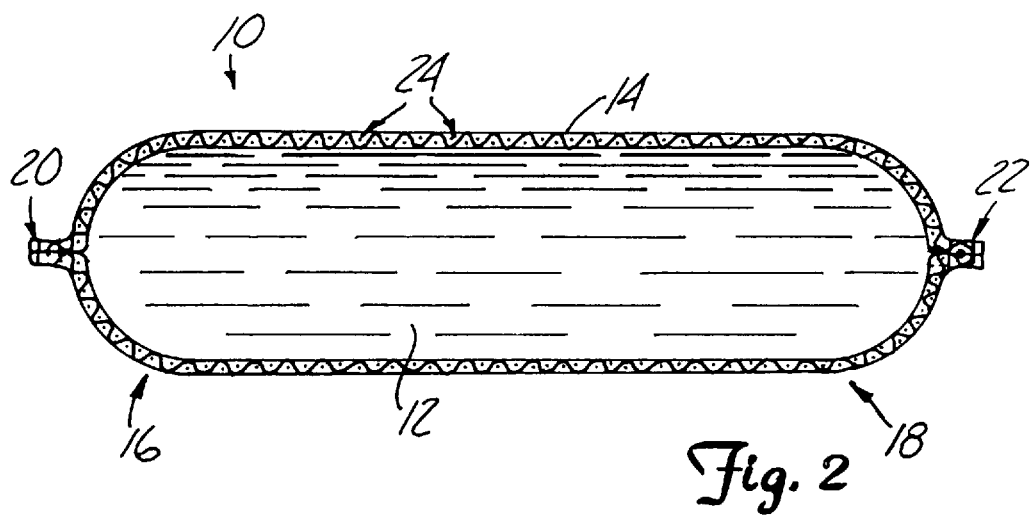
FIG. 2 is a side sectional view of the preferred prosthetic spinal disc nucleus along the line of 2—2 of FIG. 1.
Figure 3:
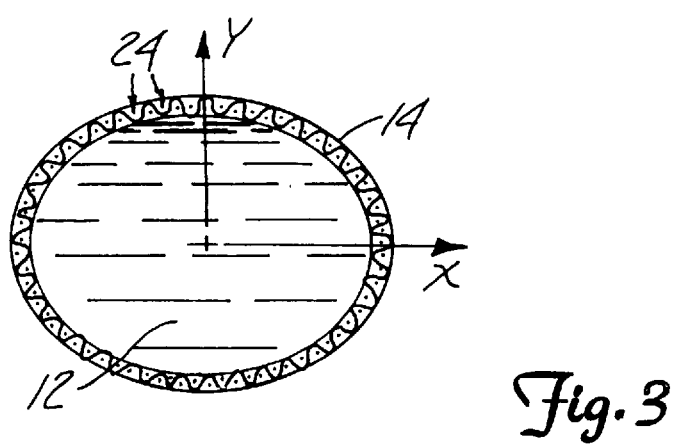
FIG. 3 is a frontal sectional view of the preferred prosthetic spinal disc nucleus along the line 3—3 of FIG. 1.

As shown in FIGS. 2 and 3, the hydrogel core 12 is fabricated to assume a pillow shape. Along the longitudinal (or sagittal) plane (as shown in FIG. 2), the hydrogel core 12 has an obround configuration whereas the frontal plane (as shown in FIG. 3) is oval. The frontal plate of the prosthetic spinal disc nucleus 10 defines a major axis ("x" in FIG. 3) and a minor axis ("y" in FIG. 3).

The hydrogel core 12 is formulated as a mixture of hydrogel polyacrylonitrile. In particular, acrylamide and acrylonitrile (block co-polymer) are used. Alternatively, the hydrogel core 12 can be any hydrophilic acrylate derivative with a unique multiblock copolymer structure or any other hydrogel material having the ability to deform and reform in a desired fashion in response to placement and removal of loads. Even further, a biologically safe polymer which can imbibe fluids while maintaining its structure under various stresses is acceptable. For example, the hydrogel core can be formulated as a mixture of polyvinyl alcohol and water. Much like a normal human nucleus, the hydrogel core 12 will initially swell as it absorbs fluid. When hydrated, the hydrogel core 12 will have a water content of between 25–90%. The hydrogel material 12 of the preferred embodiment is manufactured under the trade name Hypan® by Hymedix International, Inc.

Completely surrounding the hydrogel core 12 is the constraining jacket 14. The constraining jacket 14 is preferably a closed tube made of a tightly woven high molecular weight, high tenacity polymeric fabric. Further, the constraining jacket 14 is flexible. In a preferred embodiment, high molecular weight polyethylene is used as the weave material for the constraining jacket 14. However, polyester or any other high molecular weight, high tenacity polymeric material can be employed, and carbon fiber yarns, ceramic fibers, metallic fibers, etc., also are acceptable. In the preferred embodiment, while the constraining jacket 14 is itself flexible, the material comprising the constraining jacket 14 is not. In other words, the material making up the constraining jacket 14 has virtually no stretch.

The constraining jacket 14 is preferably made of fibers that have been highly orientated along their length. As a result, the constraining jacket 14 material has little elasticity or stretch, and defines a generally fixed volume. In the preferred embodiment, the generally fixed volume of the constraining jacket 14 is less than the volume of the hydrogel core 12 if allowed to hydrate fully without constraint. Thus, because the hydrogel core 12 has a natural volume greater than the constraining jacket 14, the constraining jacket 14 will be tight about the hydrogel core 12 when hydrated, as described in greater detail below. Finally, the volume differential between the constraining jacket 14 and the hydrated hydrogel core 12 serves to extend the useful life of the prosthetic spinal disc nucleus 10. In particular, the constraining jacket 14 effectively prevents the hydrogel core 12 from reaching its natural hydration level. Consequently, the hydrogel core 12 will have a constant affinity for imbibing more water.

The preferred woven construction of the constraining jacket 14 creates a plurality of small openings 24. These openings are large enough to allow bodily fluids to interact with the hydrogel core 12, which is maintained within the constraining jacket 14. However, the openings 24 are small enough to prevent the hydrogel 12 from escaping. Preferably, the openings 24 have an average diameter of about 10 micrometers, although other dimensions are acceptable. While the constraining jacket 14 is described as having a weave configuration, any other configuration having a semipermeable or porous attribute can be used.

The preferred woven construction of the constraining jacket 14 also provides a textured outer surface for purchase within the disc space. Thus, the constraining jacket 14 prevents the prosthetic spinal disc nucleus 10 from spontaneously dislodging from the disc space. Additionally, the constraining jacket 14 material preferably allows for tissue in-growth.

FIGS. 4–6 illustrate the manufacturing of the prosthetic spinal disc nucleus 10. First, the hydrogel core 12 is formulated. An approximately sized volume of hydrogel material is molded in a preferred geometry and then dehydrated, resulting in an undersized, substantially cylindrical gel capsule. This dehydrated hydrogel material 12 is then inserted into the constraining jacket 14.

As shown in FIG. 4, the constraining jacket 14 is preferably tubular in shape with openings at both the anterior end 16 and the posterior end 18. The hydrated hydrogel material 12 is placed within the constraining jacket 14 and centered between the anterior end 16 and the posterior end 18. The ends of the constraining jacket 14 are then secured by forming the anterior closure (not shown) and the posterior closure 22.

In the centered position, the hydrogel material core 12 will have a length smaller than that of the constraining jacket 14, resulting in excess outer layer material 26 at both the anterior end 16 and the posterior end 18. The excess outer layer material 26 at both the anterior end 16 and the posterior end 18 is closed to prevent the hydrogel material 12 from escaping or leaking from the confines of the constraining jacket 14. As shown in FIGS. 5 and 6, to form the posterior closure 22, the excess outer layer material 26 is preferably folded or tucked and then closed. The fold is created by pinching two opposing sides of the excess material 26 centrally towards one another, approximating a "figure 8" form. The two remaining free ends are flattened against one another, resulting in an "H-shaped" fold as shown in FIG. 5.

The fold is then closed by sewing a dense, bar-tack stitch 28 across the folded section at a position near the hydrogel core 12. The bar-tack stitch 28 material is preferably the same high tenacity polymeric material, such as high molecular weight polyethylene, as is used for the constraining jacket 14. By employing the same material for both the constraining jacket 14 and the bar-tack stitch 28, the biocompatibility of the entire prosthetic sinal disc nucleus 10 is ensured. The remaining excess material 26 is removed by a thermal cut made at a point distal to the bar-tack stitch 28. This thermal cut fuses the potentially fraying ends of the constraining jacket, distal to the stitched portion 28.

While FIGS. 5 and 6 only show the posterior closure 22 on the posterior end 18, the excess material 26 on the anterior end 18 is folded and sealed in a similar fashion to form the anterior closure 20. Notably, it is not always necessary to fold the excess outer layer material 26, where the anterior end 16 and the posterior end 18 are simply sealed by the dense, bar-tack stitch 28 without folding the material 26. Further, while the constraining jacket 14 has been described as having two openings, it may instead be manufactured with a single opening, either on an end or side, through which the hydrogel core 12 is inserted.

To aid in ensuring proper placement of the prosthetic spinal disc nucleus 10 within the intervertebral disc space and to review the stability of the prosthetic disc 10 during patient follow-ups, a radiopaque wire 30 is placed inside the constraining jacket 14, at either the anterior end 16 or the posterior end 18, or both or longitudinally along the length of the constraining jacket 14. The radiopaque wire 30 is visible in x-ray applications and is preferably made of a platinum-iridium material, but can be any other material having a radiopaque and biologically inert characteristics. The wire 30 is placed within the excess material 26 at the anterior end 16 or the posterior end 18 and is secured by the bar-tack stitch 28. Alternatively, a radiopaque thread can be woven into the constraining jacket 14 or a radiopaque material can be added to the hydrogel core 12.

The preferred dimensions of the prosthetic spinal disc nucleus 10 can be described at three different stages. First, after the hydrogel core 12 is hydrated but prior to conditioning; second, where the hydrogel core 12 is conditioned and hydrated, but is not subjected to any loads; and third where the prosthetic spinal disc nucleus 10 has been conditioned, hydrated and is subjected to normal loads.

In its final hydrated form and prior to conditioning (described below), the prosthetic spinal disc nucleus 10 will have a length in the range of approximately 10 to 35 millimeters and an outer diameter in the range of approximately 3 to 15 millimeters. The preferred prosthetic spinal disc nucleus 10 is 25 millimeters in length and 10 millimeters in outer diameter following hydration. These dimensions conform with the approximate length of the sagittal diameter and approximate height of an adult human disc nucleus space, respectively. It is realized that not all human discs are of the same size. Therefore, the prosthetic spinal disc nucleus 10 alternatively is constructed to assume dimensions of 20 millimeters in length and 10 millimeters in outer diameter; 25 millimeters in length and 7 millimeters in outer diameter; and 20 millimeters in length and 7 millimeters in outer diameter. Notably, other sizes are possible. The appropriate prosthetic disc for a particular patient is determined by various diagnostic procedures prior to and during surgery. Basically, the properly dimensioned prosthesis is a function of the patient's size and spinal level. By providing a prosthetic spinal disc nucleus 10 with varying dimensions, the space requirements reflected by any spinal segment, human or animal, are satisfied.

Following closure of the constraining jacket 14 about the hydrogel core 12, the prosthetic spinal disc nucleus 10 is rehydrated and then subjected to compressive loads or "conditioning". The conditioning amounts to a series of at least three compressive loads being applied across the length of the prosthetic body 10. The magnitude of in vivo compressive loads will vary from patient to patient and is a function of the patient's size and spinal level. For example, published literature has stated that the normal sitting or standing compressive load on the discal area is 1.8 multiplied by the patient's body weight. Further, the maximum compressive load placed upon the lumbar discal area during usual, daily activities is 3.6 multiplied by the patient's body weight. The conditioning, therefore, will consist of a series of compressive loads being placed upon the prosthetic spinal disc nucleus 10 equivalent to a minimum of 1.8 multiplied by the typical body weight up to a maximum of 3.6 multiplied by the typical body weight. Following conditioning, the hydrogel core 12 will consistently return to its desired shape and size following the application and removal of compressive loads.

As a result of the above-described conditioning in combination with other elements such as size, shape, etc., the hydrogel core 12 and thus the prosthetic spinal disc nucleus will have a known load bearing ability. The resulting hydrogel core is a viscoelastic, having a defined cross-sectional area and thickness, as well as a defined compression of modulus of elasticity, as shown, for example, in FIG. 7. The graph provided in FIG. 7 represents the change in height of the prosthetic spinal disc nucleus 10 in response to various loads. Due to conditioning, the hydrogel core 12, and thus the prosthetic spinal disc nucleus 10, will consistently adhere to the curve shown in FIG. 7. The conditioning ensures that the resulting hydrogel core 12 is deformable, but essentially is not compressible.

As a further benefit, the manufacturing process places a volume expansion constraint on the hydrogel core 12. Even if the hydrogel core 12 were unconstrained (e.g., if the constraining jacket 14 ruptures), following conditioning the hydrogel core 12 will not expand to more than about twice its initial volume after conditioning. Thus, a continuous, unlimited, potentially hazardous swelling of the hydrogel core 12 will not occur should the constraining jacket 14 be disrupted. This internalized constraint will also prevent possible over-expansion of the hydrogel core 12 if the prosthetic spinal disc nucleus 10 is continually unloaded in the disc space or if the prosthetic spinal disc nucleus 10 were to be displaced into another body cavity, such as the spinal canal or abdomen.

The conditioning renders the prosthetic spinal disc nucleus 10 to the flattened oval shape previously referred to in FIG. 3. For example, a hydrated prosthetic spinal disc nucleus 10 originally having a frontal cross-section diameter of about 10 millimeters will have a minor axis dimension of about 7 millimeters and a major axis dimension of about 14 millimeters following conditioning. Similarly, conditioning will alter a prosthetic spinal disc nucleus 10 having an original frontal cross-section diameter of about 7 millimeters to one having a minor axis dimension of about 5 millimeters and a major axis dimension of about 12 millimeters. It is important to note that the hydrogel core 12 is specifically designed to slightly deflect in response to loads placed upon the spinal tract. Therefore, dimensions of the hydrated, prosthetic spinal disc nucleus 10 are more properly described in terms of an unloaded and loaded state. Thus, in final, unloaded form, the prosthetic spinal disc nucleus 10 will have a hydrated frontal cross-section configuration defining a major axis diameter in the range of approximately 10–20 millimeters and a minor axis diameter in the range of approximately 5–15 millimeters.

Following conditioning, the prosthetic spinal disc nucleus 10 is dehydrated and inserted into a retaining tube to maintain the oval shape up until implantation. In the dehydrated state, the constraining jacket 14 is loose about the hydrogel core 12. The retaining tube is preferably made of implantable grade stainless steel, but can be any other surgically safe material such as polyethylene. The prosthetic spinal disc nucleus 10 and its retaining tube may be packaged in a dry foam. The entire surgical package is sterilized in a tray, via gamma, steam or other type of sterilization. Once conditioned, retained, and sterilized, the dehydrated prosthetic spinal disc nucleus 10 is ready for implantation into the human disc space.

Figure 8:
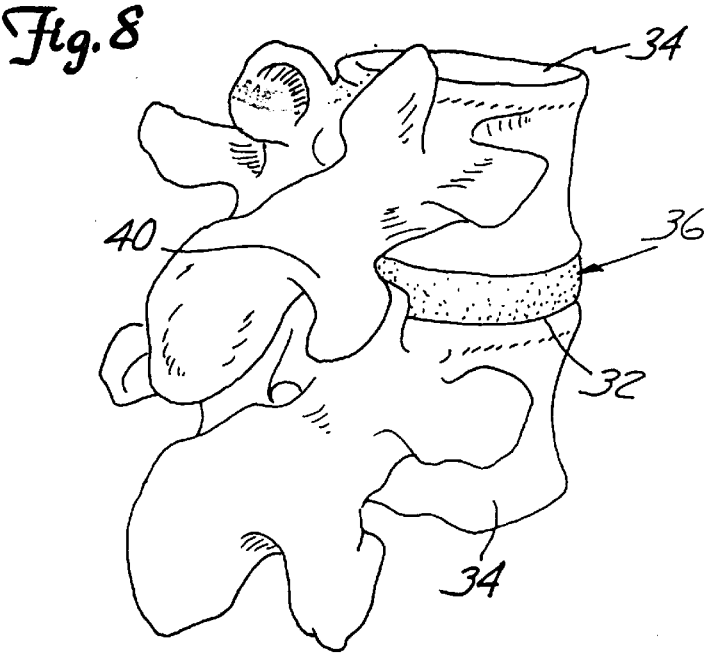
FIG. 8 is a perspective view of a spinal segment including a degenerated discal area.
Figure 9:
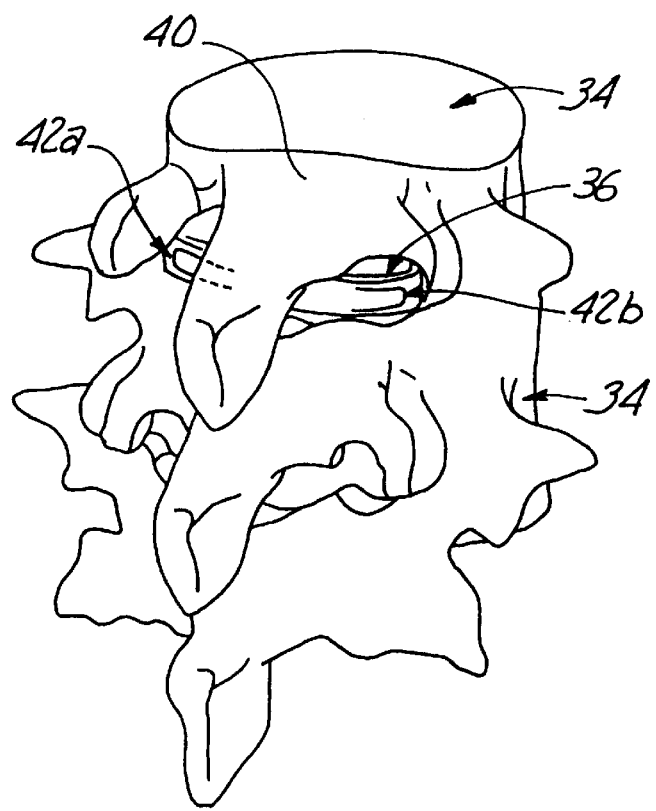
FIG. 9 is a posterior view of a human spine showing two flaps that have been cut through an anulus.

As shown in FIGS. 8, 9 and 10 the prosthetic spinal disc nucleus 10 is preferably inserted in pairs into a damaged disc space 32. The disc space 32 separates two adjacent vertebrae 34 and includes an anulus 36 and a nucleus region 38 (shown in FIG. 10). Proper positioning is achieved by performing a laminotomy in a targeted lamina area 40. A pair of flaps 42a and 42b are created in the anulus 36 and, if necessary, excess material is removed from the nucleus region 38 to create room for the prosthetic spinal disc nucleus 10. The flaps 42a and 42b have a height less than the minor axis dimension of the prosthetic spinal disc nucleus body 10. In a preferred embodiment, the flaps 42a and 42b have a length of about 12 millimeters and a height of about 6 millimeters for use with a prosthetic body having a minor axis diameter of 7 millimeters. Importantly, due to the preferred flattened shape of the prosthetic spinal disc nucleus 10, the flaps 42a and 42b need not encompass the entire height of the anulus 36. Although in this example, a pair of flaps 42a and 42b are illustrated and discussed, a single flap may alternatively be used.

The vertebrae 34 adjacent the damaged disc space 32 are then slightly separated. This slight separation can be achieved by inserting an inflatable jack through one of the flaps 42a or 42b and jacking apart the adjacent vertebrae 34. Once separation sufficient to insert a prosthetic spinal disc nucleus 10 is achieved, the flap 42a or 42b not occupied by the jack has a prosthetic spinal disc nucleus 10 inserted via a tapered holding tube. The jack is then deflated and removed, and a second prosthetic spinal disc nucleus 10 is placed through the remaining flap 42a or 42b. Once implanted, the hydrogel core 12 of the prosthetic spinal disc nuclei 10 begin to hydrate, imbibing surrounding fluids. To promote an increase in the rate of hydration, saline or similar fluid is injected or flushed into the nucleus area. Finally, the flaps 42a and 42b are sewn into their original position.

When properly implanted, the anterior end 16 of each of the prosthetic spinal disc nuclei 10 will be adjacent to and inside of the anterior end of the anulus 36; the posterior end 18 will be adjacent to and inside of the posterior end of the anulus 36. By imparting the flaps 42a and 42b with a height dimension smaller than that of the prosthetic nuclei 10 and closing the flaps 42a and 42b after implant, a positive fixation within the anulus 36 is provided and likewise the retropulsion of the prosthetic spinal disc nuclei 10 from the anulus 36 is prevented. Further, the preferred constraining jacket 14 is preferably textured to maintain the position of the prosthetic spinal disc nucleus 10 by providing a grip or purchase with tissue of the end plates (not shown).

Figure 11A:
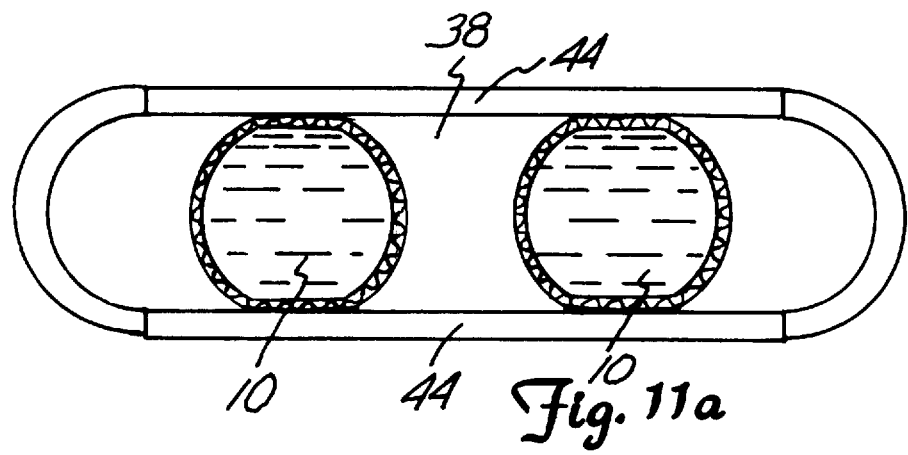
FIGS. 11A and 11B are enlarged, side section views of a human disc space having two prosthetic spinal disc nuclei under load.

Following implantation, each of the prosthetic spinal disc nuclei 10 function as an intervertebral spacer and a cushion, and restores the normal fluid pump action of the disc space 32. By employing a flexible woven material for the constraining jacket 14, the hydrogel core 12 is allowed to deform and reform in a controlled fashion in response to physiological loads. Following implant, as the hydrogel core 12 imbibes fluid, the constraining jacket 14 has sufficient flexibility to allow the hydrogel core 12 to expand. However, the strength and flexibility characteristics of the material used for the constraining jacket 14 are such that the general shape of the hydrogel 12 will always be maintained. As the hydrogel core 12 hydrates, its volume increases significantly. At a certain, predetermined hydration point, the hydrogel core 12 reaches the volume limits of the constraining jacket 14, which becomes tight. Because the constraining jacket 14 has a relatively fixed circumference, the constraining jacket 14 forces the hydrogel core 12 to become more circular, thus increasing in the direction of the minor axis (y in FIG. 3), as more fluids are imbibed. Thus, the constraining jacket 14 works in concert with the hydrogel core 12 to control expansion of the prosthetic spinal disc nucleus 10 after implant. Once hydrated, the prosthetic spinal disc nucleus 10 will still have an oval shaped frontal cross-section, but will be more circular than prior to hydration. As shown in FIGS. 11A and 1iB, the prosthetic spinal disc nucleus 10 will not expand to a completely circular frontal cross-section due to forces imparted by the vertebral end plates 44, 46 and conditioning of the hydrogel core 12 prior to implant.

Following implant and hydration, the prosthetic spinal disc nucleus 10 will deform and reform in response to the placement and removal of loads on the disc space. The prosthetic spinal disc nucleus 10 flattens in response to placement of physiological loads on the spine, thus assuming a more flattened shape, and acts as a cushion against various loads placed upon it. As these loads are decreased (e.g., when the patient reclines), the hydrogel core 12 reforms back in a predetermined fashion to its original shape, due to the conditioning process described above. To prevent the hydrogel core 12 from escaping, the constraining jacket 14 preferably has a burst strength which is greater than the swelling pressure of the hydrogel core 12 when fully hydrated. Effectively, the constraining jacket 14 directs the hydrogel core 12 to swell or expand vertically within the nucleus region 38. This controlled swelling pushes apart or further separates the vertebrae 34 adjacent to the disc space 32, as would a normal nucleus.

Figure 11B:
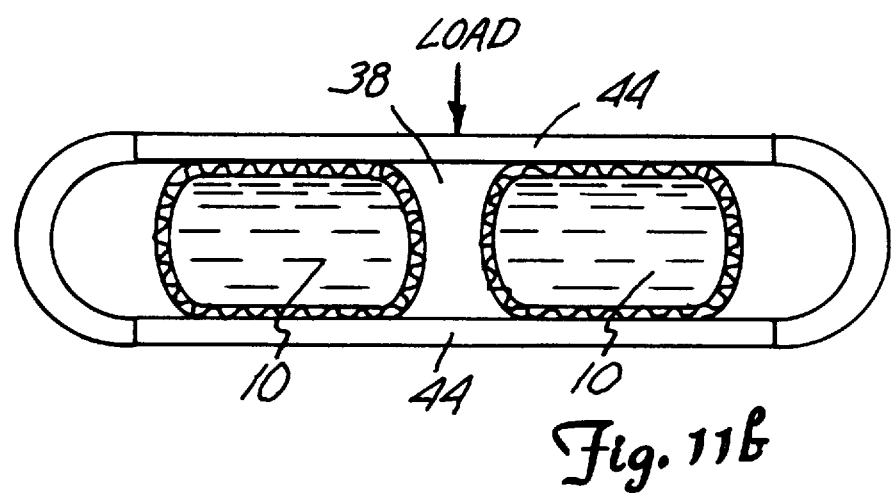

The prosthetic spinal disc nuclei 10 also restore the natural fluid pumping action of the disc space 32. The hydrated prosthetic spinal disc nuclei 10 occupy a certain percentage, but not all of, the nucleus region 38. The nucleus region 38 is defined by the anulus 36 and the vertebral end plates 44, 46 above and below the nucleus region 38, respectively. The vertebral end plates 44, 46 are attached to the adjacent vertebrae 34 (FIG. 8) above and below the disc space 32. In FIG. 11A, the disc space 32 is unloaded (e.g., when the patient is reclining). As the loads on the disc space 32 increase, the prosthetic spinal disc nuclei 10 cushion the vertebral end plates 44, 46 and thus the adjacent vertebrae 34 (FIG. 8) and slowly deform. As a result, the volume within the nucleus region 38 decreases. In other words, a load placed upon the disc space 32 forces the vertebral end plates 44, 46 toward one another, as shown in FIG. 11B. This action reduces the overall volume of the nucleus region 38, as the vertebral end plates 44 are closer together, while the anulus 36 stretches only slightly. Notably, because the prosthetic spinal disc nuclei 10 do not occupy the entire nucleus region 38, there is room for the respective hydrogel cores 12 to deform (FIG. 11B), and the reduction in volume of the nucleus region 38 is allowed to take place as would otherwise occur with a normal nucleus. If the entire nucleus region 38 were filled by the prosthetic spinal disc nuclei 10, they would prevent the vertebral end plates 44 from naturally moving toward one another in response to the load. The hydrogel core 12 of each prosthetic spinal disc nucleus 10 will flatten or deform, but not decrease in volume, in a predetermined fashion in response to the load. Because the prosthetic spinal disc nuclei 10 essentially do not decrease in volume, and the overall volume of the nucleus region 38 has been reduced, the prosthetic spinal disc nuclei 10 now occupy a larger percentage of the nucleus region 38. As a result of the reduction in space, fluids otherwise found in the nucleus region 38 are forced out of the disc space 32, thus flushing out the accumulated acids or autotoxins contained therein.

Conversely, when the load is removed or decreased, the prosthetic spinal disc nuclei 10 reform in a predetermined fashion, moving toward their original, unloaded shape (shown in FIG. 11A). This entails an increase in the vertical direction (with reference to the orientation of FIGS. 11A and 11B), causing the vertebral end plate 44, 46 to separate. Notably, if the hydrogel core 12 of each of the prosthetic spinal disc nuclei 10 were unable to reform to its original shape, the disc space 32 would remain in the flattened position shown in FIG. 11B upon removal or decrease of the load, instead of returning to the natural state shown in FIG. 11A. Separation of the vertebral end plates 44, 46 creates an increased volume in the nucleus region 38. The hydrogel core 12 of each of the prosthetic spinal disc nuclei 10 does not increase in volume, it simply reforms. As a result, bodily fluid, containing beneficial nutrients, fills the now increased volume of the nucleus region 38, revitalizing the overall disc space 32. Thus, the prosthetic spinal disc nuclei 10 act in concert with the natural disc space 32 to restore the natural pumping action of the disc space 32.

Notably, the hydrogel core 12 of the present invention independently absorbs the force/pressure placed on the disc space 32. Thus, the anulus 36 is not required to support the force/pressure from the hydrogel core 12. The anulus 36 does not provide any circumferential support to the prosthetic spinal disc nucleus 10.

While the preferred embodiment has described the prosthetic spinal disc nucleus 10 as being sized for implant along the sagittal diameter of the nucleus region 38, other sizes and orientations are equally acceptable. More particularly, as shown in FIG. 12, an alternative embodiment provides a prosthetic spinal disc nucleus 100a or 100b with a length approximating the transverse diameter of the nucleus region 38. Preferably, the prosthetic spinal disc nucleus 100a or 100b has a width which is less than one-half of the sagittal diameter so that two prosthetic disc nuclei 100a and 100b can be implanted, side-by-side. Notably, the alternative prosthetic spinal disc 100a or 100b are implanted utilizing the same surgical method previously described, including creating one or more flaps 42a, 42b in the anulus 36 and rotating the prosthetic spinal disc nucleus 100a and 100b after insertion into the nucleus region 38.

Another alternative embodiment of a prosthetic spinal disc nucleus 110 is shown in FIG. 13. To assist in preventing the retropulsion implant, the prosthetic spinal disc nucleus 10 can be provided with a tine assembly 150 located on the external surface of the prosthetic spinal disc nucleus 110. When properly oriented, the tine assembly 150 will promote the simple implantation of the prosthetic spinal disc nucleus 110 into the disc space, but greatly inhibits removal or spontaneous retropulsion. The tine assembly 150 provides an additional fixation of the prosthetic spinal disc nucleus 110 within the disc space.

The tine assembly 150 is attached to a posterior end 118 of the prosthetic spinal disc nucleus 110 and projects away from an external face of a constraining jacket 114. Each individual tine 152 on the tine assembly 150 has an approximately triangular shape, including a base 154 and an end 156. The base 154 of each tine 152 is integrally attached to a frame 158 of the tine assembly 150. Each tine 152 projects laterally away form the tine assembly frame 158 in an angular fashion. In other words, when the tine assembly 150 is properly oriented on the prosthetic spinal disc nucleus 10, each individual tine 152 projects away from the constraining jacket 114 in a direction rearward with respect to the anterior end 116 and outward with respect to the anterior end 118.

The tine assembly 150 is preferably made of the same high molecular weight, height tenacity polymeric material, such as polyethylene, as is used for the constraining jacket 14. By employing a material of this type, the tine assembly 150, and therefore each individual tine 152, will have desired strength and flexibility characteristics required for proper implantation of the prosthetic spinal disc nucleus 110. Prior to and during implant, the tine 152 material has sufficient flexibility to allow each tine 152 to fold down against the external surface of the constraining jacket 114. When implanted, the tine 152 material has a resiliency which forces each tine 152 to assume the angular position shown in FIG. 13. In this expanded position, each tine 152 has a strength characteristic which will prevent the retropulsion of the prosthetic spinal disc nucleus 110 from its implantation position and provides a positive fixation within the anulus.

The tine assembly 150 has been described as preferably having individual tine bodies 152 extending from the frame 158. Each tine 152 is equally spaced from one another, providing uniform support to the prosthetic spinal disc nucleus 110 when placed within the anulus. However, any number or configuration of tines 152 can be used which also provide a solid fixation within the anulus and prevent retropulsion.

During manufacture, once an anterior closure 120 and a posterior closure 122 have been formed, the tine assembly 150 is attached to the prosthetic spinal disc nucleus 110. The tine assembly 150 is slid over the posterior end 118 and secured to the constraining jacket 114 by frictional or mechanical fastening or sewing, which may include a hook and loop configuration, or adhesive.

An additional means for retarding expulsion is the potential use of tapered collars secondarily attached to the constraining jacket 114 by way of sewing or spin entanglement. Such collars would collapse against the constraining jacket 114 on insertion of the prosthetic spinal disc nucleus 110 and flare on attempted removal or forceful expulsion from the annular confines.

Figure 14:
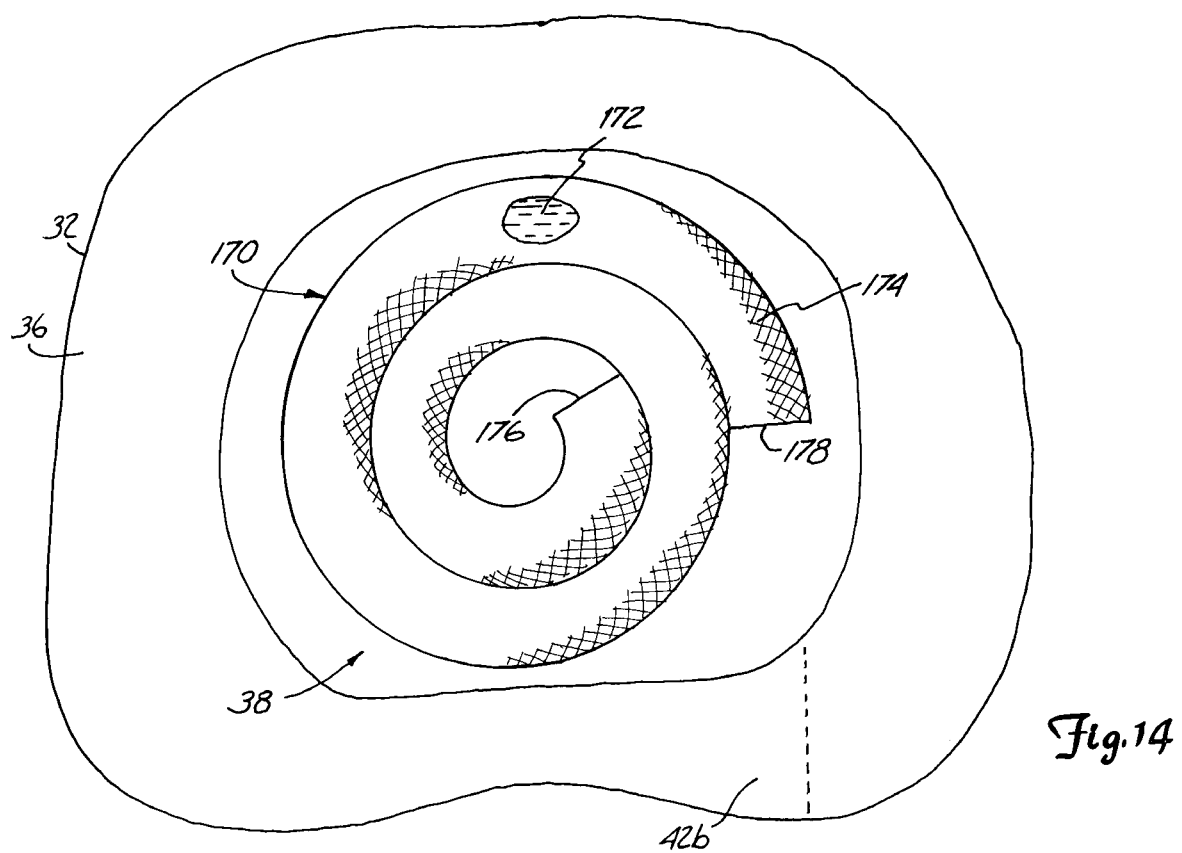
FIG. 14 is a top, sectional view of a human disc space having an alternative prosthetic spinal disc nucleus implanted.

Yet another alternative embodiment of a prosthetic spinal disc nucleus 170 implanted in the disc space 32 is provided in FIG. 14. The prosthetic spinal disc nucleus 170 is similar to previous embodiments and includes a hydrogel core 172 surrounded by a constraining jacket 174. The prosthetic spinal disc nucleus 170 is further defined by a first end 176 and a second end 178.

Similar to previous embodiments, the hydrogel core 172 is preferably conditioned prior to implant. In addition to creating a known load bearing ability in the hydrogel core 172, the conditioning also creates a spiral-shape memory or bias in the hydrogel core 172. As shown in FIG. 14, the hydrogel core 172 is biased such that in a relaxed state, it forms a coil or spiral. Importantly, following conditioning, the hydrogel core 172 can be uncoiled, but is biased to return to the coiled position.

In one preferred embodiment, the hydrogel core 172 is approximately rectangular-shaped in cross-section, having a height of approximately 8.2 mm and a width of approximately 4.1 mm. Further, when coiled as shown in FIG. 14, the prosthetic spinal disc nucleus 170 has an overall width of approximately 25 mm. Obviously, other dimensions are equally acceptable so long as the hydrogel core 172 has a height great enough to adequately separate two adjacent vertebrae, and the prosthetic spinal disc nucleus 170 has an overall width sufficiently sized to support adjacent vertebrae.

The prosthetic spinal disc nucleus 170 is implanted in the nucleus region 38 of the disc space 32 in a manner highly similar to that previously described. In particular, the flap 42b is imparted in the anulus 36. Notably, only one flap is required. The flap 42b is retracted, exposing the nucleus region 38 from which excess material is removed, if necessary. The prosthetic spinal disc nucleus 170 is then passed through the opening (not shown) in the anulus 36 created by the flap 42b. In this regard, the prosthetic spinal disc nucleus 170 is first at least partially uncoiled and the first end 176 is passed through the opening created by the flap 42a. The remainder of the prosthetic spinal disc nucleus 170 is then fed through the opening created by the flap 42b. The previously described shape memory of the hydrogel core 172 cause the prosthetic spinal disc nucleus 170 to reform to the coil shape within the nucleus region 38. Importantly, because the prosthetic spinal disc nucleus 170 can be uncoiled prior to implant, only a small opening in the anulus 36 is required.

The prosthetic spinal disc nucleus of the present invention: a) restores the height of the damages disc space, b) restores and tightens the natural anulus to stop further degeneration and permit its healing, c) restores the normal load-unload cycling and thus flushes out toxic by-products, bringing in fresh nutrients to the nucleus and anulus, d) allows a near normal range of motion, e) relieves the movement-induced discogenic pain of the vertebral segment, and f) allows the use of a minimal, posterior surgical procedure that provides both cost and medical benefits. The device of the present invention can be implanted with a high degree of certainty that the required dimensions presented by the damaged disc space will be maintained following insertion of the discal nucleus device.

Although the present invention has been described with reference to preferred embodiments, workers skilled in the art will recognize that changes may be made in form and detail without departing from the spirit and scope of the invention. For example, other methods of sealing the ends of the jacket exist such as heat, ultrasound, crimp ring seals or spin entanglement. Additionally, more than a single layer of material may be used to maintain the integrity of the hydrogel core. In other words, a plurality of jackets can surround the hydrogel core.

The hydrogel itself can have an outer "skin" formed by ion implantation which causes outer layer crosslinking and functions as the jacket or as an interposed membrane between the gel mass and the jacket. Alternatively, expansion and contraction of the hydrogel core can be achieved via the use of a hydrogel which readily expels fluids. Further, other means exist for limiting expansion and contraction in the major axis of the frontal cross-section of the hydrogel core without the use of a separate jacket. For example, a truss can be embedded along the sides of the hydrogel core. The truss is perpendicular to the major axis of the hydrogel core and effectively creates an anisotropic scenario in which the hydrogel core is allowed to expand solely in the direction of the minor axis when a load is removed. Similarly, the hydrogel core will contract only in the direction of the minor axis in response to placement of a load. Other tine or circumferential collar configurations exist which act to prevent retropulsion of the prosthetic spinal disc nucleus, including the anterior end. Finally, the prosthetic spinal disc nucleus can be used in all areas of the spine, and can be implanted in animals, such as in the disc space of a dog or the ankle of a horse.

What is claimed is:

1. A prosthetic spinal disc nucleus for implantation into a human disc space having a nucleus region defined by an anulus and adjacent vertebral end plates, the prosthetic spinal disc nucleus comprising:

a hydrogel core having an oval-shaped frontal cross-section defining a major axis and a minor axis, wherein the hydrogel core is configured to expand from a dehydrated state to a hydrated state; and a constraining jacket surrounding the hydrogel core, wherein the constraining jacket maintains the hydrogel core in the hydrated state at a major axis diameter in the range of approximately 10–20 millimeters and a minor axis diameter in the range of approximately 5–15 millimeters.

2. The prosthetic spinal disc nucleus of claim 1 wherein the constraining jacket has a textured outer surface for providing purchase within the disc space.

3. The prosthetic spinal disc nucleus of claim 1 wherein the constraining jacket maintains the hydrogel core at a length in the range of approximately 10–30 millimeters in the hydrated state.

4. The prosthetic spinal disc nucleus of claim 1 wherein the major axis diameter of the hydrogel core is 15 millimeters in the hydrated state.

5. The prosthetic spinal disc nucleus of claim 1 wherein the minor axis diameter of the hydrogel core is 10 millimeters in the hydrated state.

6. The prosthetic spinal disc nucleus of claim 1 wherein the constraining jacket has a volume which is less than the volume of the hydrogel core when completely hydrated.

7. The prosthetic spinal disc nucleus of claim 1 wherein the hydrogel core is configured to have a predetermined compression modulus of elasticity in the hydrated state.

8. The prosthetic spinal disc nucleus of claim 1 wherein the nucleus region has a loaded volume when a load is placed upon the disc space and an unloaded volume when the load is decreased, the loaded volume being less than the unloaded volume, and further wherein the hydrogel core is configured to force fluid from the nucleus region after implantation in response to the load placed upon the disc space.

9. The prosthetic spinal disc nucleus of claim 8 wherein the hydrogel core occupies a first percentage of the loaded volume of the nucleus region and a second percentage of the unloaded volume of the nucleus region, the second percentage being less than the first percentage.

10. The prosthetic spinal disc nucleus of claim 1 wherein the hydrogel core has a predetermined frontal cross-sectional area in the hydrated state, and further wherein the hydrogel core is configured such that following implant, the predetermined frontal cross-sectional area will not change in response to a load placed upon the disc space.

11. The prosthetic spinal disc nucleus of claim 1 wherein the hydrogel core is configured to have a predetermined shape in the hydrated state, and further wherein the hydrogel core is configured to deform in response to a load placed upon the disc space and reform to the predetermined shape after removal of the load.

12. The prosthetic spinal disc nucleus of claim 1 wherein the jacket is substantially inelastic and has a fixed circumference for directing the hydrogel core to expand in the minor axis diameter.

13. A prosthetic spinal disc nucleus for implantation into a human disc space having a nucleus region defined by an anulus and adjacent vertebral end plates, the prosthetic spinal disc nucleus comprising:

a hydrogel core having an oval-shaped frontal cross-section defining a major axis and a minor axis, wherein the hydrogel core is configured to deform from an unloaded state to a loaded state; and a constraining jacket surrounding the hydrogel core, wherein the constraining jacket maintains the hydrogel core in the loaded state at a minor axis diameter in the range of approximately 3–10 millimeters.

14. An incompressible, elastic, deformable and reformable spinal disc nucleus prosthesis, including a core surrounded by a jacket, implanted within a nucleus cavity having a variable volume defined by an anulus and a pair of spaced vertebral end plates, the prosthesis having a fixed volume following completion of implantation that is less than the volume of the nucleus cavity, a height which decreases with increasing load on the end plates and which increases with decreasing load on the end plates to allow for corresponding variation in volume of the nucleus cavity so that when the volume of the nucleus cavity decreases with increasing load on the end plates, a pressure within the nucleus cavity is increased to force fluid out of the nucleus cavity, and when the volume of the nucleus cavity increases with decreasing load on the end plates, the pressure within the nucleus cavity is decreased to draw fluid into the nucleus cavity.

* * * * *